(12) United States Patent
Finch et al.

(10) Patent No.: US 7,858,932 B2
(45) Date of Patent: Dec. 28, 2010

(54) CAPILLARY EMITTER FOR ELECTROSPRAY MASS SPECTROMETRY

(75) Inventors: Jeffery W. Finch, Gig Harbor, WA (US); Jennifer H. Granger, Chandler, AZ (US)

(73) Assignee: Waters Technologies Corporation, Milford, MA (US)

( * ) Notice: Subject to any disclaimer, the term of this patent is extended or adjusted under 35 U.S.C. 154(b) by 776 days.

(21) Appl. No.: 10/598,799

(22) PCT Filed: Mar. 25, 2005

(86) PCT No.: PCT/US2005/010069
§ 371 (c)(1), (2), (4) Date: May 21, 2007

(87) PCT Pub. No.: WO2005/096720
PCT Pub. Date: Oct. 20, 2005

(65) Prior Publication Data
US 2007/0267293 A1 Nov. 22, 2007

Related U.S. Application Data

(60) Provisional application No. 60/557,410, filed on Mar. 29, 2004.

(51) Int. Cl.
*H01J 49/10* (2006.01)
(52) U.S. Cl. ...................... 250/288; 250/282
(58) Field of Classification Search ............... 250/282, 250/288; 422/100; 347/87; 436/180
See application file for complete search history.

(56) References Cited

U.S. PATENT DOCUMENTS

| 3,840,758 | A | * | 10/1974 | Zoltan ......................... 310/328 |
| 4,025,928 | A | * | 5/1977 | Hou et al. ...................... 347/87 |
| 4,519,751 | A | * | 5/1985 | Beckman et al. ............ 417/322 |
| 5,306,412 | A | | 4/1994 | Whitehouse et al. |
| RE34,757 | E | | 10/1994 | Smith et al. |
| 5,965,883 | A | * | 10/1999 | Lee et al. ..................... 250/288 |

(Continued)

FOREIGN PATENT DOCUMENTS

JP 61-103928 5/1986

(Continued)

OTHER PUBLICATIONS

Ionization within a Cylindrical Capacitor: Electrospray without an Externally Applied High Voltage; Houle Wang and Murray Hackett;Anal. Chem. 1998, 70, 205-212.

(Continued)

*Primary Examiner*—Nikita Wells
*Assistant Examiner*—Johnnie L Smith
(74) *Attorney, Agent, or Firm*—Jamie H. Rose; Anthony J. Janiuk (57) ABSTRACT

Disclosed herein is an electrospray device for mass spectrometry that includes a fluid inlet, an outlet orifice, and a passage for fluid communication between the fluid inlet and outlet orifice. This passage is formed from a capillary (i.e., a first capillary). This first capillary (3) partially houses a second capillary (7) such that the outlet orifice is narrowed. A portion (17) of the second capillary extends beyond the first capillary. This extension permits a practitioner to clip away obstructed portions of the second capillary.

29 Claims, 7 Drawing Sheets

U.S. PATENT DOCUMENTS

| | | | |
|---|---|---|---|
| 6,127,680 | A | 10/2000 | Andrien, Jr. et al. |
| 6,140,640 | A * | 10/2000 | Wittmer et al. .............. 250/288 |
| 6,232,129 | B1 * | 5/2001 | Wiktor ....................... 436/180 |
| 6,337,480 | B1 | 1/2002 | Andrien et al. |
| 6,395,183 | B1 | 5/2002 | Valaskovic et al. |
| 6,670,607 | B2 * | 12/2003 | Wood et al. .................. 250/288 |
| 2002/0003209 | A1 * | 1/2002 | Wood et al. .................. 250/282 |
| 2002/0060288 | A1 | 5/2002 | Hughey et al. |
| 2002/0125426 | A1 | 9/2002 | Hirabayashi et al. |
| 2002/0150511 | A1 * | 10/2002 | Wiktor ....................... 422/100 |
| 2002/0175281 | A1 | 11/2002 | Valaskovic |
| 2003/0034407 | A1 | 2/2003 | Gangl et al. |
| 2005/0029442 | A1 | 2/2005 | Takats et al. |
| 2005/0133713 | A1 | 6/2005 | Brennen |

FOREIGN PATENT DOCUMENTS

| | | |
|---|---|---|
| JP | 62-228159 A | 10/1987 |
| JP | 63-286326 | 11/1988 |
| JP | 02-132371 A | 5/1990 |

OTHER PUBLICATIONS

Nanoelectrospray Mass Spectrometry Using Non-metalized, Tapered (50-10um) Fused-silica Capillaries; James C. Hannis and David C. Muddiman; Rapid Comm. Mass Spectrom, 12, 443-448 (1998)un.

Disposable Emitters for On-line Capillary Zone Electrophoresis/Nanoelectrospray Mass Spectrometry; Kevin P. Bateman, et al.; Rapid Commun. In Mass Spectrom, vol. 11, 307-315 (1997).

Long-Lived Metallized Tips for Nanoliter Electrospray Mass Spectrometry; Gary A. Valaskovic, et al; Am Soc Mass Spectrom 1996, 7, 1270-1272).

Gold-coated fused-silica sheathless electrospray emitters based on vapor-deposited titanium adhesion layers; Nilsson, et al. Rapid Commun. In Mass Spectrom, 2003; 17; 1535-1540.

Nanoscale LC-MS: technical design and applications to peptide and protein analysis; Meiring, et al.; J. Sep. Sci. 2002,25-557-568.

* cited by examiner

CAPILLARY EMITTER FOR ELECTROSPRAY MASS SPECTROMETRY

CROSS REFERENCE RELATED APPLICATION INFORMATION

This application claims priority from U.S. Provisional Patent Application No. 60/557,410, filed Mar. 29, 2004. The contents of these applications are incorporated herein by reference.

FIELD OF THE INVENTION

In general, this invention pertains to nano/electrospray technology. In particular, the present invention relates to nano/electrospray emitters.

BACKGROUND OF THE INVENTION

Electrospray ionization ("ESI") has revolutionized the use of mass spectrometry in bioanalytical chemistry because of its ability to transfer large macromolecules from solution into the gas-phase as intact multiply-charged molecular ions. A special advantage of ESI is the ease with which it may be coupled to liquid chromatography ("LC"), capillary electrophoresis ("CE"), and capillary electrochromatography ("CEC"). An attractive development in recent years has been the design of methods for decreased sample consumption in ESI by using much lower flow rates (nL/min) than with conventional ESI (µL/min). Of these low flow ESI methods, the flow rate is controlled by some type of pump in microspray and flow-through nanospray, whereas in static nanospray the flow rate is controlled by the potential difference between the emitter and counter-electrode, and some gas pressure may also be applied to maintain the spray, where flow from the tip is typically 30-60 nL/min. Typically, nanospray emitters have been fabricated by pulling silica or glass substrates under heat to produce tapered emitters with small inner diameters, e.g., a few µm.

For nanospray ESI-MS emitters to be useful in coupling to either LC, CE or CEC, the emitters must remain stable throughout the separation process. Failure of the emitter during the course of the separation is not acceptable. For quantification in particular, if calibration curves of multiple analytes at multiple concentration levels are to be constructed, single emitters with longer lifetimes or multiple emitters showing reproducible performance and ionization efficiency are needed. The stationary bed must remain secure throughout the lifetime of the column apparatus.

While nanospray provides an avenue to achieve low-level detection limits with MS using only a few µL of sample, even at high salt and/or buffer concentrations, most nanoliter-flow ESI emitters suffer from short operating lifetimes, poor durability, and/or low reproducibility. Additionally, if the internal diameter of the emitter is too large, or there is too much dead volume associated with coupling the emitter to the outlet of the column, then band broadening can often be a problem thereby compromising effective analysis.

Presently, there is a need for an emitter that can overcome the deficiencies in the art as currently practiced.

BRIEF SUMMARY OF THE INVENTION

The present invention relates to a device that can be used as a nanospray emitter. The device includes a fluid inlet, an outlet orifice, and a passage for fluid communication between the fluid inlet and outlet orifice. In one aspect of this embodiment, the passage facilitating fluid communication between the inlet and outlet elements is comprised of a capillary column (i.e., a first capillary) that partially houses a second capillary. In one aspect, the first and second capillaries are comprised of fused silica.

The device of the present invention comprises a capillary column (or first capillary) packed with a stationary phase. The column has a fluid inlet and an outlet orifice. In this embodiment, a second capillary is disposed within a portion of the outlet. This second capillary is secured using an adhesive disposed between a portion of the exterior surface of the second capillary and a portion of the interior surface of the first capillary. In this embodiment, a portion of the second capillary protrudes from the outlet orifice of the first capillary. As this protruding portion of the second capillary becomes clogged, a practitioner can cleave off distal portions thereby relieving the second capillary free of the obstruction.

The device of the present invention includes a capillary column (or first capillary) packed with a stationary phase. The first capillary has a fluid inlet and outlet orifice. In this embodiment, a second capillary is disposed along the fluid inlet and another second capillary is disposed along the outlet orifice.

The present invention also relates to a method of separating analytes which includes passing a solution including an analyte through a capillary column of the present invention under conditions effectively separate the analytes contained within a sample. The column comprises a first capillary. This first capillary comprises a stationary phase. A second capillary, whose outer diameter is less than the inner diameter of the first capillary, is disposed partially within the first capillary near the outlet. A portion of second capillary extends beyond the first capillary. The analytes enter the column and differentially interact with functional groups of the stationary phase. The analytes can then be eluted from the column using an appropriate mobile phase.

The present invention further relates to a method of manufacturing a nanospray emitter and/or column of the present invention. Two capillaries are obtained in order to manufacture the device of the present invention. A first capillary is used to receive a second capillary. The second capillary, whose outer diameter is less than the first capillary's outer diameter, is threaded into the first capillary. Next, a stationary phase is packed within the first capillary.

DETAILED DESCRIPTION OF THE INVENTION

The present invention relates to a nanospray emitter including an emitter body which includes a fluid inlet, an outlet orifice, and a passage for fluid communication between the fluid inlet and outlet orifice. In one aspect of this embodiment, the passage facilitating communication between the inlet and outlet elements is comprised of a capillary column (i.e., a first capillary) that partially houses a second capillary. In one aspect, the first and second capillaries are comprised of polyimide-coated fused silica. However, other suitable materials are also envisaged to be within the scope of this invention including, but not limited to, ceramic glasses, borosilicate glasses, cladded fused silica, fused silica glasses, aluminosilicate glasses, quartz, metals such as stainless steel, titanium, nickel, gold, platinum, other conductive materials and alike.

Figure 1:
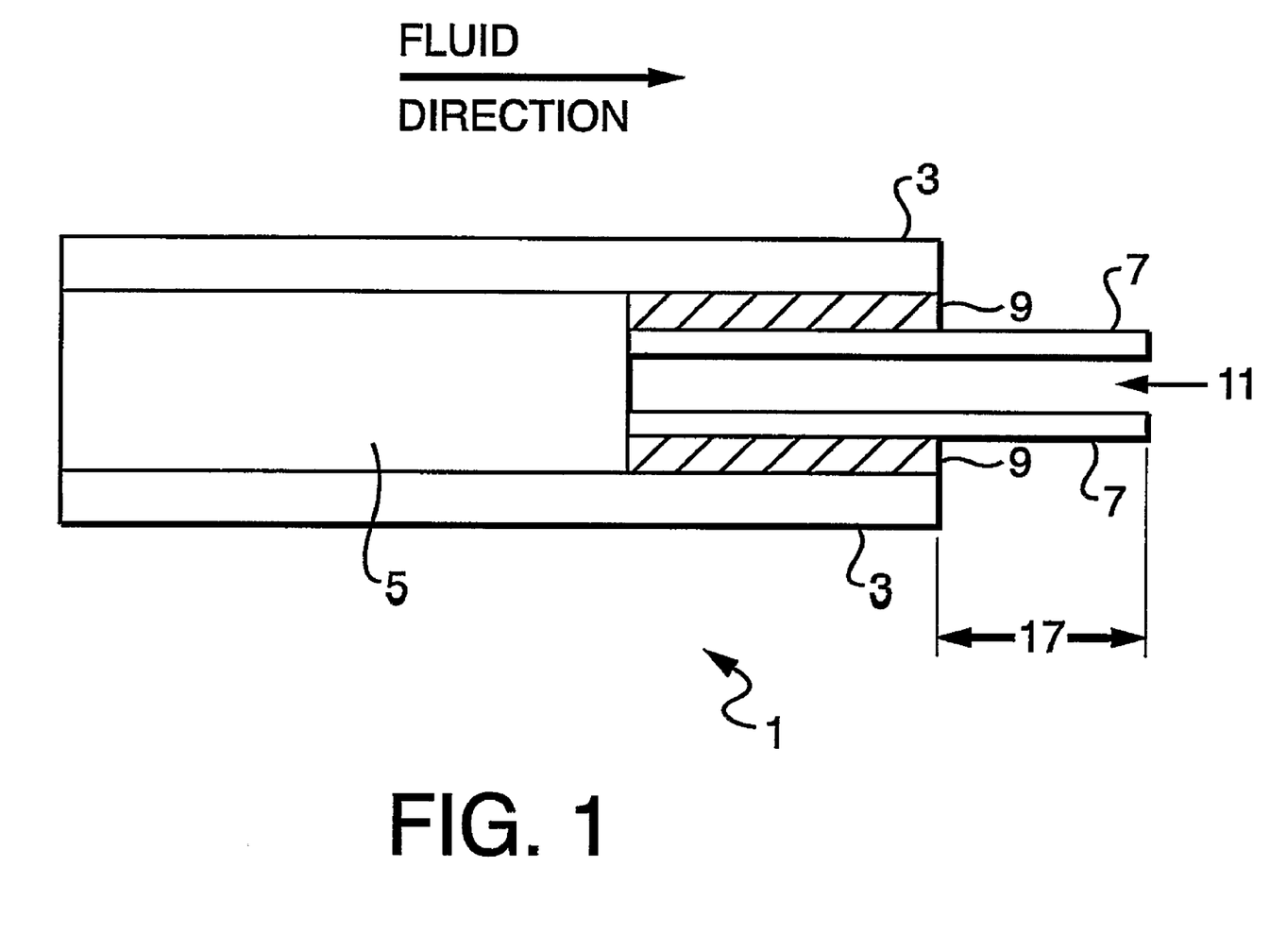
FIG. 1 illustrates a capillary column together with a nanospray emitter of the present invention.

FIG. 1 depicts one embodiment of the present invention. This figure depicts a section of a chromatography column 1 comprising a first capillary 3 and a stationary phase 5. The first capillary 3 can be comprised of polyimide-coated fused silica tubing. However, other suitable materials are also envisaged to be within the scope of this invention including, but not limited to, ceramic glasses, borosilicate glasses, fused silica glasses, cladded fused silica (such as PEEKsil™) glass-lined stainless steel aluminosilicate glasses, stainless steel, nickel, platinum, titanium, other conductive materials and alike. In one aspect, the first capillary 3 has an outer diameter from about 360 µm to about 720 µm with an inner diameter of about 100 µm to about 150 µm. The length of the first capillary ranges from about 1 cm to about 100 cm. The stationary phase 5 can comprise any suitable material well known to those skilled in the art.

The capillary column 1 of FIG. 1 also comprises a second capillary 7. This second capillary 7 can be comprised of fused silica. In this case, the fused silica is polyimide-coated. However, other suitable materials are also envisaged to be within the scope of this invention including, but not limited to, ceramic glasses, borosilicate glasses, fused silica glasses, aluminosilicate glasses, nickel, platinum, gold, other conductive materials and alike. The second capillary 7 is disposed near or at the outlet orifice of the capillary column 1. The second capillary 7 is disposed within the interior lumen of the first capillary 3. In one aspect, the secondary capillary 7 terminates internally at or near the junction with the stationary phase 5.

An adhesive material, such as poly(dimethylsiloxane) or "PDMS," can be used to secure positioning of the second capillary 7 within the first capillary 3. The adhesive material can be disposed between the external surface of the second capillary 7 and the interior (or luminal facing) surface of the first capillary 3. A preferred PDMS is sold under the trade name SYLGARD® 184 Silicone Elastomer (Dow Corning Corporation, Midland, Mich., USA). PDMS is sold as a two part elastomer usually mixed in certain ratios of base and curing agent. A preferred mixture has a ten to one ratio of base to curing agent and is used without dilution and without degassing. The second capillary 7 can have an outer diameter ranging from about 40 µm to about 150 µm with an inner diameter ranging from about 30 µm to about 5 µm. An outlet orifice 11 is still present with the second capillary 7. Obviously, the diameter of the outlet orifice 11 is reduced when a second capillary 7 is present. The length of the second capillary ranges from about 1 cm to about 10 cm.

In one aspect, the first capillary 3 can be a metal and the second capillary 7 can be, for example, fused silica. Metals that can be used include, but are not limited to, nickel, platinum, stainless steel, gold and alike. In this aspect, the metal surface of the first capillary should be oxidized in, for example, a plasma oven prior to threading the second capillary and the addition of an adhesive such as PDMS. In another aspect, the first capillary 3 is a section of fused silica, where the fused silica is cladded with a protective material which improves the rigidity and flexibility. PEEKsil™, for example, can be used as the first capillary 3, which is polymer sheathed fused silica tubing.

In one aspect of this embodiment, the second capillary 7 protrudes from the first capillary 3 in the area of the outlet. This protrusion can be from about 30 mm to about 1 mm. This protruding portion 17 is contiguous with the rest of the second capillary 7. As the outlet becomes obstructed, a practitioner can cleave a small section of the protruding portion 17 containing the obstruction in such a manner so as to relieve the obstruction within the second capillary 7 and restore original flow.

The second capillary 7 can be prepared in a similar fashion as the first capillary 3, these techniques are well known to those skilled in the art. Once the second capillary 7 is constructed it can be threaded into position within the lumen of the first capillary 3. Obviously, the outer diameter of the second capillary 7 is less than the inner diameter of the first capillary 3. An adhesive agent, such as PDMS, can be used to secure the second capillary 7 into position within the first capillary 3. Heat can be applied in order to effectuate fusion of the two capillaries (i.e., first and second capillary). Temperatures ranging from about room temperature (~25° C.) to about 110° C. are applied to cure the PDMS.

In one aspect, a conductive coating can be applied the capillary column 1. In a particular aspect, the coating is added to the first capillary 3. In another particular aspect, the coating is added to the second capillary 7. In yet another aspect, the coating is added to both the first capillary 3 and the second capillary 7. This coating facilitates high voltage connection between an energy source and the capillary column 1. Examples of suitable coating materials include, but are not limited to, carbon, gold, nickel, titanium, platinum, stainless steel, polyaniline (PANI), polypropylene (including a polypropylene/graphite mixture), polyimide/graphite, and other conductive materials.

The coating can be applied by use of any method well known to those skilled in the art. For example, the capillary apparatus, or at least the portion that is going to be coated, can be dipped into a soluble suspension containing the desired coating. This suspension can either be an aqueous solution or organic solvent. After dipping, the solvent is allowed to evaporate leaving behind the desired coating on the portion of the capillary apparatus dipped into the suspension. See WO 01/50820, the entire teaching of which is incorporated herein by reference. Further, by way of example, a thin layer of a conductive material is deposited on a portion of the capillary apparatus by electrolytic deposition, sputter coating, electrochemical deposition or vapor deposition. See: Nilsson et al, "Gold-coated fused silica sheathless electrospray emitters based on vapor deposited titanium adhesion layers", *Rapid Comm. in Mass Spectrom.* 203:17 1535-1540.

It is believed that some suitable electrically conductive coatings of the present invention additionally exhibit electrostatic adherence to the capillary substrate, such as glass. For example, it is very likely that PANI coatings possess positively charged sites within the polymer that interact with negatively charged sites on the substrate.

In one aspect of the present invention, the thickness of the electrically conductive coating is substantially uniform over the entire or a portion of the capillary apparatus (comprising capillary one and two). In one aspect, the thickness of the electrically conductive coating is less than about 10 µm. In a particular aspect, the thickness of the coating is from about 2 µm to about 4 µm. In another particular aspect, the thickness of the coating is from about 25 nm to about 100 nm. In yet another aspect, the thickness of the coating is from about 100 nm to about 2 µm.

The conductive coating can be applied to any portion of the capillary apparatus which will facilitate electrical charge to be conveyed to the solution passing through the capillary. For example, the coating can be applied to the entire or a portion of the first capillary, alternatively, the coating can be applied to the entire or a portion of the second capillary, and in yet another alternative, the coating can be applied to both the first and second capillaries. The conductive coating can be applied to a portion of the capillary apparatus adjacent to an inlet, such as the inlet of the first capillary. The conductive coating can be applied to an outlet portion, such as the outlet of the second capillary.

Coating with PANI is characterized by the following properties: high resistance to electrical discharge, with coatings lasting for several days or more under electrospray conditions; a conductivity of about 5 S/cm at 25° C. and 1 M HCl (MacDiarmid et al., Synth. Met. (1987) 18, 190-285); resistance to corrosion (Wessling and Posdorfer, Electrochim. Acta (1999) 44, 2139-2147) while maintaining mechanical stability and antistatic properties (Triveldi and Dhawan, J. Mat. Chem. (1992) 2, 1091-1096); optical transparency (green), allowing for direct viewing of an ESI sample; and outstanding adherence to glass properties (Manohar et al., Synth. Met. (1991) 41-43, 711-714), the entire teachings of which are incorporated herein by reference.

Returning to FIG. 1, a mobile phase can traverse the present invention in accordance with the vector provided in the figure. The flow rate of the mobile phase ranges from about 50 µL/min to about 20 nL/min or less. As the mobile phase traverses the stationary phase 5 within the column 1, specific interactions can occur between the analytes contained within the mobile phase and the functional groups of the stationary phase 5. The mobile phase exits the stationary phase 5 and enters the outlet area of the column 1.

Figure 2:
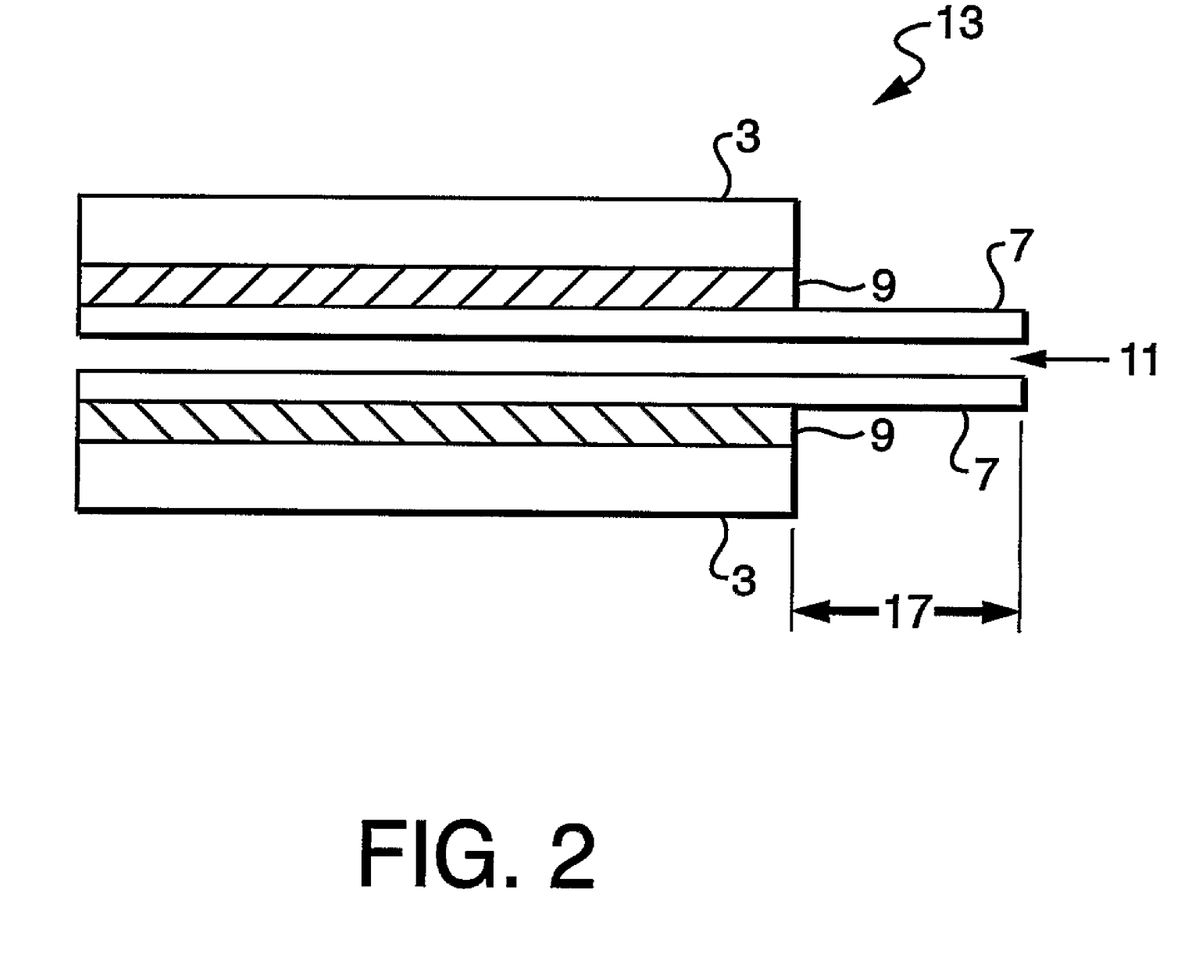
FIG. 2 illustrates a nanospray emitter of the present invention.

FIG. 2 illustrates a nanospray emitter 13 of the present invention. The emitter 13 comprises a first capillary 3 and a second capillary 7. In this embodiment, the second capillary 7 is partially housed within the first capillary 3. The first 3 and second 7 capillaries are comprised of a suitable material including, but not limited to, polyimide-coated fused silica, ceramic glasses, borosilicate glasses, aluminosilicate glasses, gold, titanium, platinum, nickel, other conductive materials and alike. Additionally, a conductive coating, such as gold, carbon, polyaniline coating and alike can be applied to coat the emitter. In one aspect of this embodiment, both the first 3 and second 7 elements are comprised of fused silica. The second capillary 7 is held securely within the first capillary 3 by an adhesive agent 9. In one aspect, the adhesive agent 9 is PDMS.

By including a second capillary 7 within the first capillary 3, the outlet orifice is reduced. The reduction in both outer an inner diameters of the outlet orifice ranges from a factor of about 4 to about 10 For example, in one aspect, the diameter of the first capillary 3 can be around 360 µm while the outer diameter of the second capillary 7 can be about 90 µm. In this aspect, there is a reduction in diameter of about a factor of 4. The inner diameter for the first capillary is about 75 µm while the inner diameter for the second capillary 7 is about 10 µm.

Also depicted in FIG. 2 is a portion of the second capillary 7 protruding 17 from the blunt end of the first capillary 3. The amount in which the second capillary 7 protrudes 17 is relative. Initially, the protruding portion 17 can extend from the blunt end of the first capillary 3 from about 1 to about 30 mm. (It should be understood, however, that the secondary capillary extends interiorly the full length of the emitter region.) However, as the apparatus is used over time, conceivably the second capillary 7 will become obstructed with material. Should the obstruction occur inside the exposed (or perhaps "protruding") portion of the second capillary near the tip, then a practitioner can remove the portion of the second capillary 7 that is obstructed using any means well known to those skilled in the art. By removing the obstruction, the original flow is restored.

Figure 3:
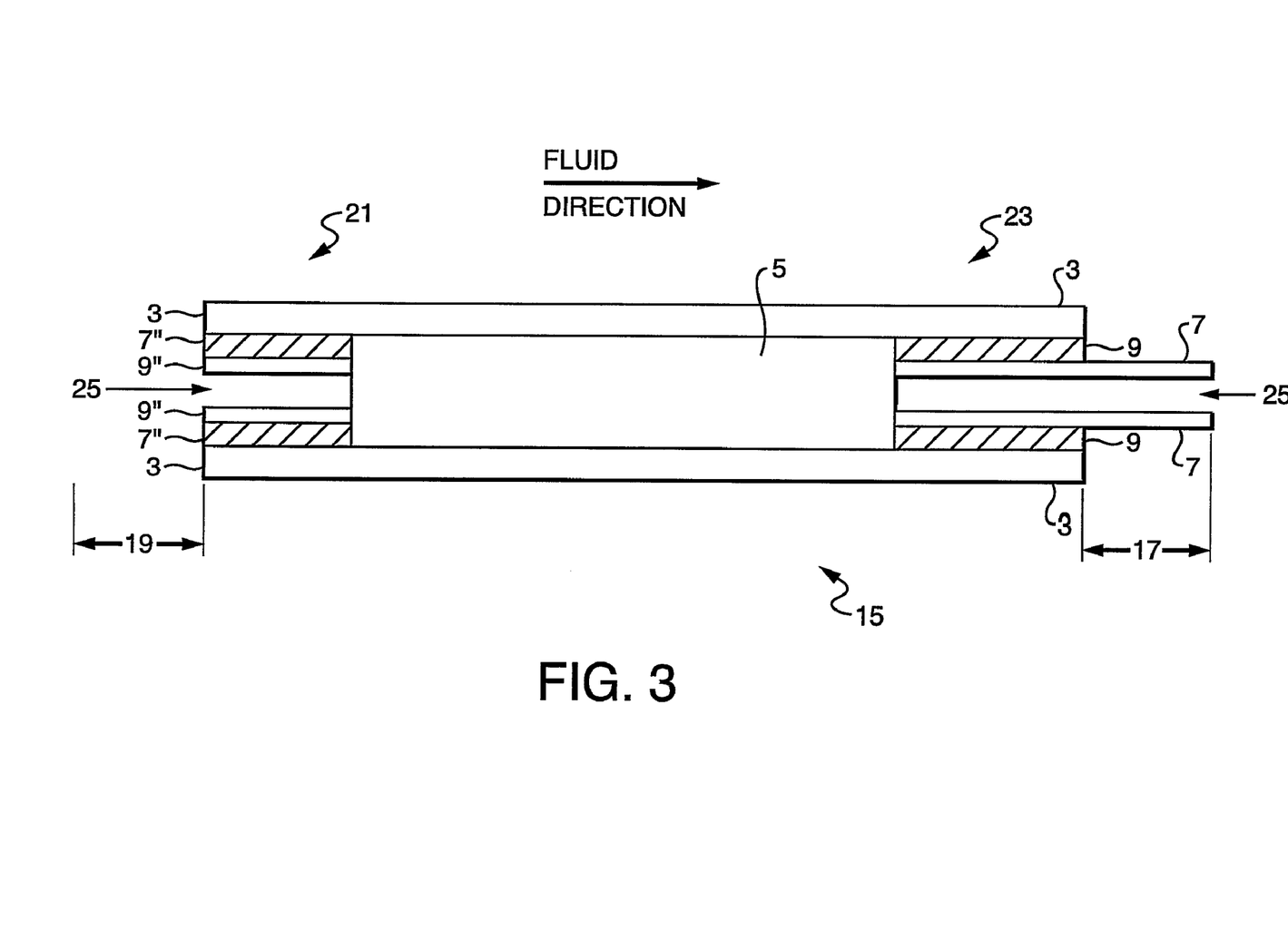
FIG. 3 illustrates one embodiment of the present invention.

FIG. 3 depicts another embodiment of the present invention. In this embodiment, a column 15 comprises a stationary phase 5, an inlet 21, and outlet 23 In this embodiment, a capillary within a capillary, each capillary essentially as depicted in FIG. 2, is disposed at both the inlet 21 and outlet 23 ends of the column 15. In an alternative embodiment of the invention, the inlet end 21 could be open, with no inner capillary secured in place to retain the stationary phase bed. The stationary phase at the inlet end 21 could also be secured in place using a frit, or other means well known to those skilled in the art.

Referring to the inlet 21 portion of the column, a second capillary 7" is disposed within a first capillary 3. In one aspect, both the second 7" and first 3 capillaries are comprised of polyimide-coated fused silica. Other suitable materials can be used as previously mentioned. The second capillary 7" is held securely in place within the first capillary 3 by an adhesive agent 9". In one aspect, this adhesive agent 9" is PDMS.

Shown in FIG. 3 is a protruding portion 19 of the second capillary 7". In one aspect, there is no protruding portion 19 of the second capillary 7" issuing forth from the inlet 21, thereby making that end a blunt end. In other words, the second capillary 7" is flush with the first capillary 3.

The inner diameter of the inlet orifice 25 created by the second capillary 7" can range from about 10 µm to about 20 µm. There are several advantages to having the inlet 21 constructed using a second capillary disposed within a first capillary. For example, this construction can assist in securing the stationary phase within the column. Additionally, by narrowing the internal diameter, via the second capillary 7", band broadening tends to diminish.

The outlet portion 23 of the column has a similar appearance as the embodiment depicted in FIG. 1. There is a first capillary 3 that, as FIG. 3 illustrates, traverses the entire longitudinal axis of column 15 essentially providing the outer shell of the column 15. As with the inlet portion 21, a second capillary 7 is disposed within the first capillary 3. The second capillary 7 is held securely in place within the first capillary 3 with an adhesive agent 9. In one aspect, the adhesive agent is PDMS. With the second capillary 7 in place, the outlet orifice 27 is narrowed to about 10-20 µm. Typically, the inlet and outlet inner diameters are equivalent, though they need not be.

FIG. 3 illustrates a protruding portion 17 of the second capillary 7. This portion 17 of the second capillary extends beyond the first capillary 3. The length of this protruding portion 17 can range from about 1 to about 30 mm. As the tip becomes obstructed with use, a practitioner can remove the section of second capillary 7 containing the obstruction, thereby restoring the original flow.

A method of separating a sample of analytes using a capillary column of the instant invention is disclosed herein. The sample of one or more analytes is admixed under suitable conditions using an appropriate mobile phase. This mobile phase is a solvent in which the analytes are capable of being solubilized. The mobile phase-containing analytes is then introduced into a chromatography system. This chromatography system comprises a capillary column of the present invention. The columns of the instant invention comprise a first and second capillary in which the second capillary in either fully or partially housed within the first capillary. The first capillary also comprises a stationary phase. This stationary phase has functional groups that can interact with analytes. The analytes, when introduced into the column, traverse the stationary phase contained within the first capillary interacting with the functional groups of the stationary phase. Some analytes will have more affinity for the functional groups than others, depending upon the conditions present (contributed by the mobile phase). Differential separation and elution of the analytes can then be performed using a suitable elution solvent.

The exiting effluent (comprising one or more analytes) can be an introduced into a detection system such as a mass spectrometer by means of nano-electrospray where a liquid junction is utilized to apply high voltage to the effluent. This mode of analysis can be with or without a nebulizing sheath. In another aspect, the analytes can be subjected to a capillary electrophoresis unit coupled with an emitter of the present invention. In yet another aspect, the analytes can be subjected to capillary electrochromatography unit coupled with an emitter of the present invention. These are standard modes of analysis well known to those skilled in the art. (See Kennedy, R. T., et al., Chem. Rev. (1999) 99, 3081-3131.)

The instant invention also pertains to methods for making a nanospray device. A first capillary is obtained. This capillary can be comprised of any suitable material, as mentioned above. In one aspect, the first capillary is comprised of fused silica. A second capillary is then obtained. The second capillary can be comprised of the same material as that of the first capillary, or it can be comprised of another suitable material. This second capillary has a narrower outer diameter than the first capillary's inner diameter such that it can be threaded within the inner diameter of the first capillary. The second capillary is securely held in position using an adhesive agent, such as PDMS. Heat can be applied in order to effectuate fusion of the two capillaries (i.e., first and second capillary). Temperatures ranging from about room temperature (~25° C.) to about 110° C. can be applied. Next, the first capillary is packed with a predetermined stationary material (see, e.g., U.S. Pat. No. 5,997,746, the entire teaching of which is incorporated herein by reference), or a monolithic phase is synthesized and prepared inside the first and/or second capillaries by those skilled in the art.

EXAMPLES

Example 1

Figure 4:
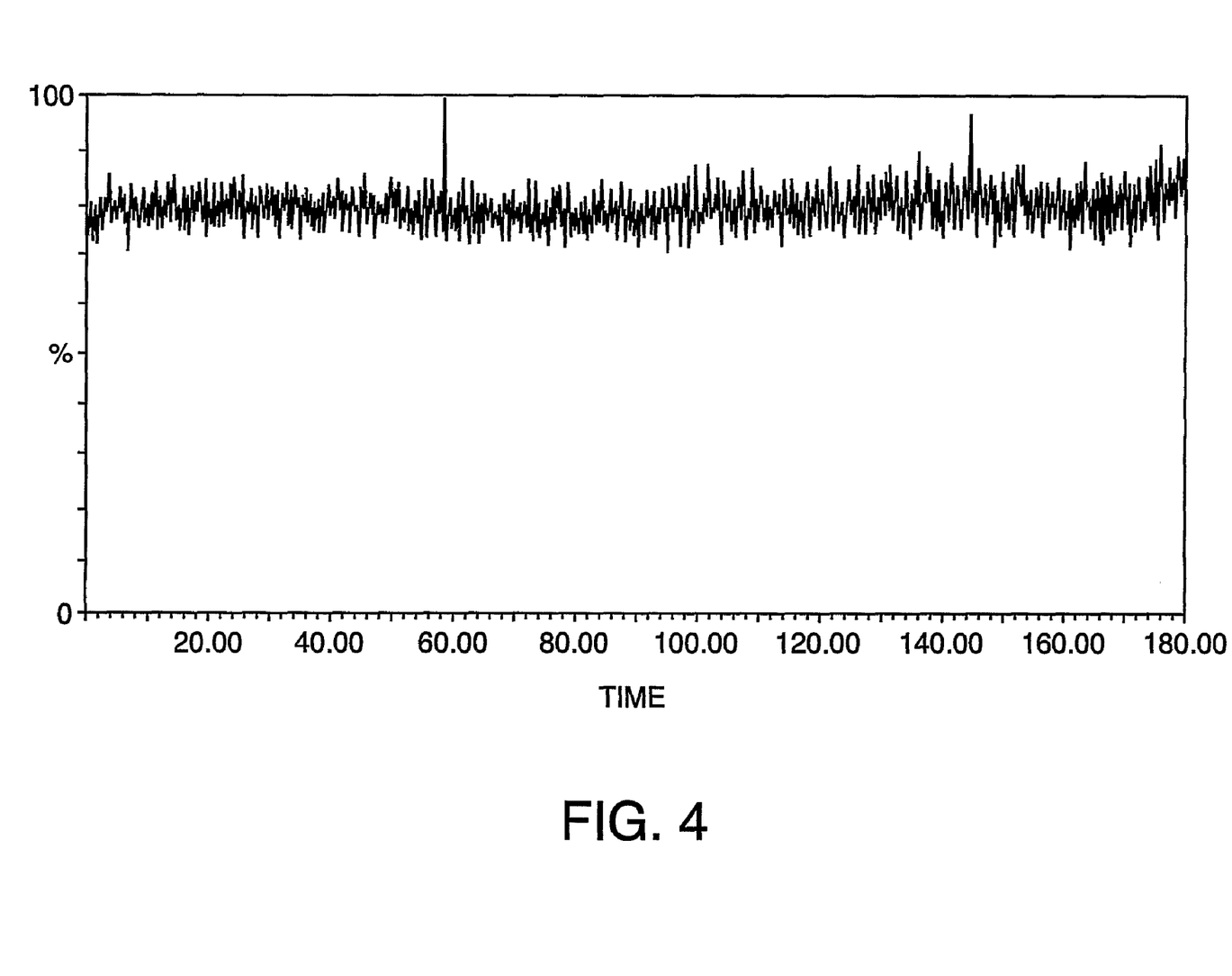
FIG. 4 is a total ion chromatogram illustrating the stability of a PDMS fabricated nanospray emitter of the present invention.

Demonstration of the Stability of the Nanospray Emitter of the Present Invention FIG. 4 illustrates a Total Ion Chromatogram (TIC). The instant TIC illustrates the stability of a PDMS fabricated nanospray emitter (20 μm id) for an infusion of 400 femtomole/μL solution of [Glu$^1$]-Fibrinopeptide B, at a flow rate of 400 nL/min over a period of three hours. Data was acquired using a Micromass Q-Tof Micro™ quadrupole/TOF hybrid instrument with a nanospray Z-spray source housing. Capillary voltage (applied at liquid junction) was 3.5 kV, solvent is 1:1 water/acetonitrile with 0.1% formic acid.

Example 2

Reproducible Behavior of the Nanospray Emitter of the Present Invention

Figure 5A:
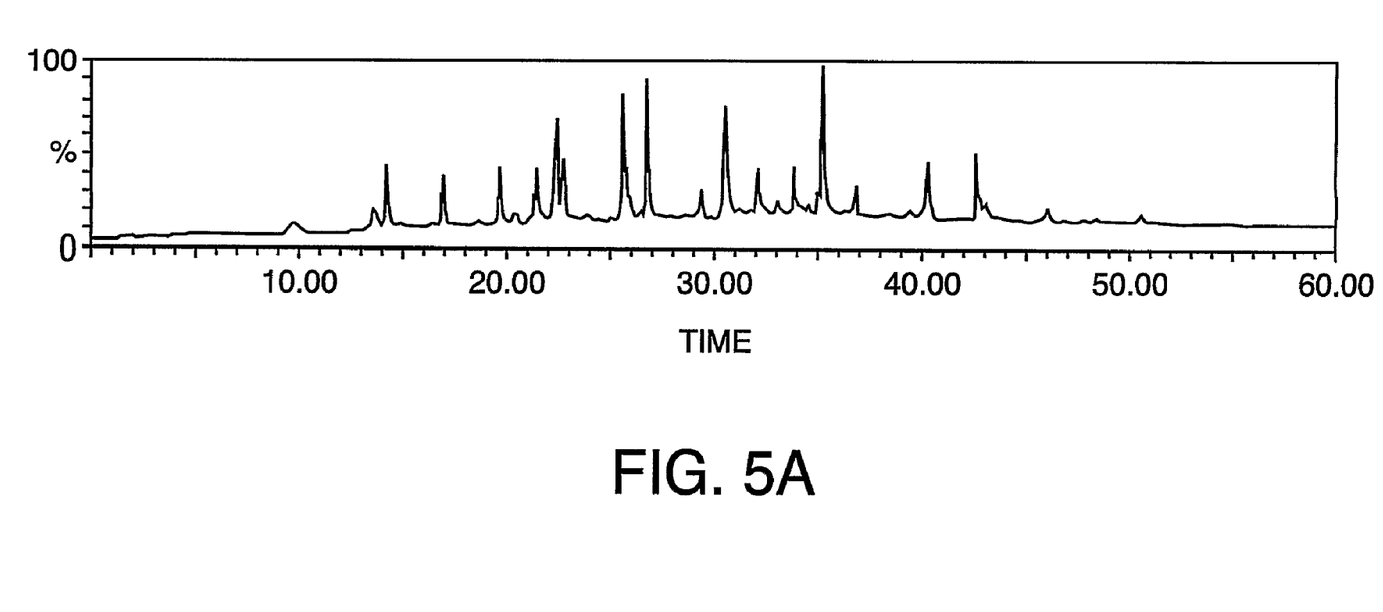
FIG. 5A, 5B and 5C illustrates three chromatograms obtain from three repeat injections of sample.
Figure 5B:
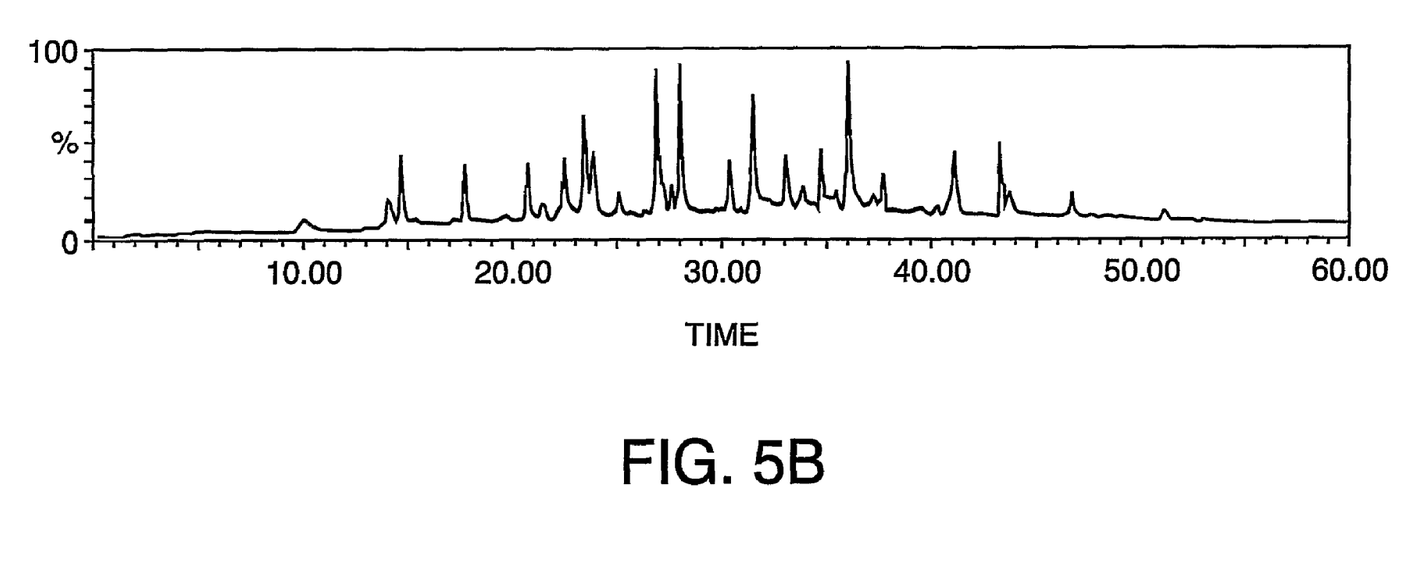
Figure 5C:
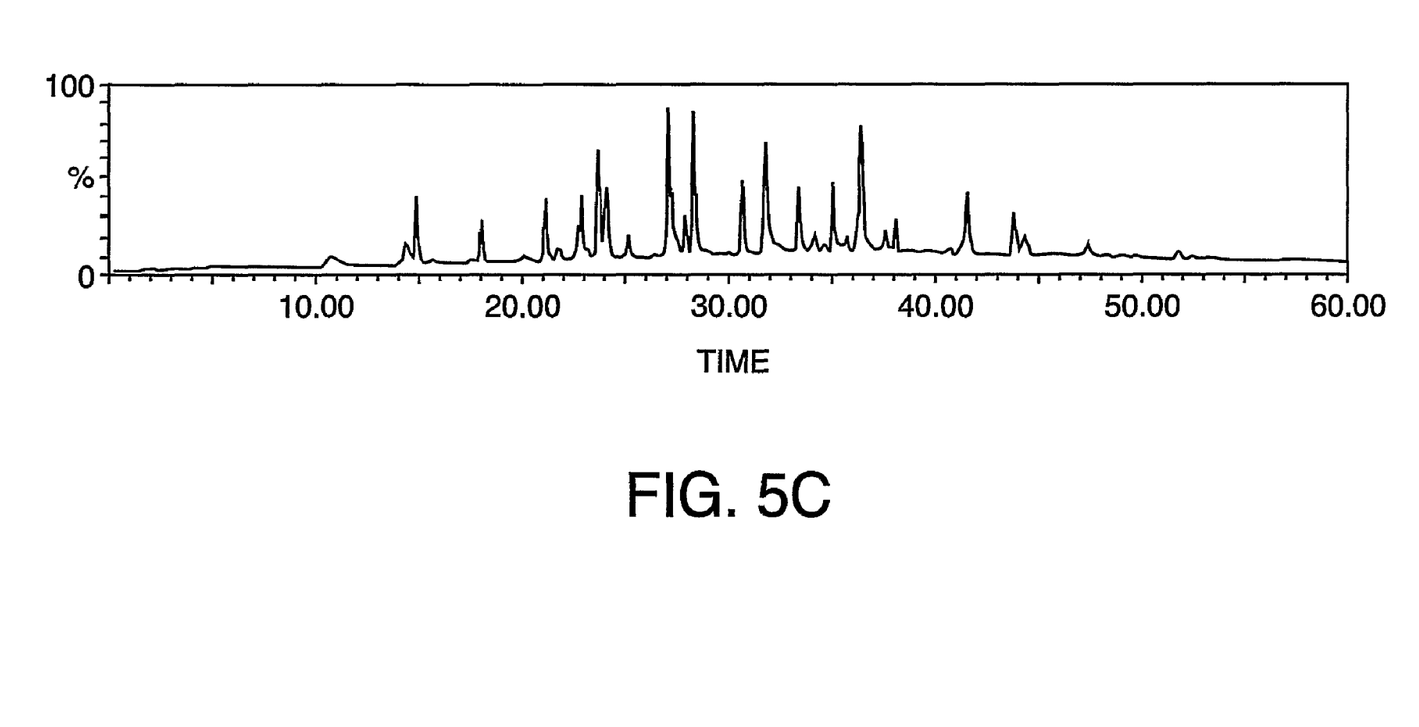

FIG. 5A, 5B and 5C illustrates LC/MS chromatograms of three repeat injections of 500 femtomoles of an enolase digest, using a 20 μm id PDMS fabricated emitter coupled to a Waters Symmetry® C18 NanoEase™ column (75 μm×100 mm, 5 μm particle size). A Waters CapLC™ HPLC system was utilized with a flow rate=430 nL/min (split from 4 μL/min), solvent A: 0.1% formic Acid, solvent B: 98% acetonitrile/2% water with 0.1% formic acid, gradient: 5% B to 50% B in 60 minutes. Data was acquired using a Micromass Q-Tof Micro™ quadrupole/TOF hybrid instrument with a nanospray Z-spray source housing. Capillary voltage (applied at liquid junction) was 3.5 kV. Total continuous run time of the three injections is over 5.5 hours.

Although the invention has been described with respect to various embodiments, it should be realized this invention is also capable of a wide variety of further and other embodiments within the spirit and scope of the appended claims.

What is claimed is:

1. A capillary column, comprising
a first capillary and a second capillary,
a stationary phase packed in the first capillary,
wherein said second capillary is disposed partially within said first capillary,
wherein said second capillary is securely positioned within said first capillary using an adhesive agent, and
wherein a portion of said second capillary protrudes from said first capillary.

2. The capillary column of claim 1, wherein said first capillary comprises a material selected from the group consisting of polyimide-coated fused silica, cladded fused silica, PEEKsil™, glass-lined stainless steel, ceramic glass, borosilicate glass, aluminosilicate glass, stainless steel, nickel, platinum, titanium, and polypropylene.

3. The capillary column of claim 1, wherein said second capillary comprises a material selected from the group consisting of polyimide-coated fused silica, cladded fused silica, glass-lined stainless steel, ceramic glass, borosilicate glass, aluminosilicate glass, stainless steel, nickel, platinum, titanium, and polypropylene.

4. The capillary column of claim 2, wherein said first and said second capillaries comprise polyimide-coated fused silica.

5. The capillary column of claim 1, wherein said adhesive agent is PDMS.

6. The capillary column of claim 1, wherein said second capillary protrudes from said first capillary by approximately 1 to 30 mm.

7. The capillary column of claim 1, wherein said first capillary has an inner diameter of about 100 μm.

8. The capillary column of claim 1, wherein said second capillary has an inner diameter ranging from about 2 μm to about 20 μm.

9. The capillary column of claim 1, wherein said second capillary has an inner diameter ranging from about 2 μm to about 10 μm.

10. The capillary column of claim 1, wherein said first capillary has an outer diameter of about 360 μm.

11. The capillary column of claim 1, wherein said second capillary has an outer diameter of about 90 μm.

12. The capillary column of claim 1 further comprising a coating material.

13. The capillary column of claim 12, wherein said coating material is selected from the group consisting of gold, nickel, titanium, platinum, carbon, polyaniline, polypropylene, and polypropylene/graphite.

14. The capillary column of claim 12, wherein said first capillary is coated.

15. The capillary column of claim 12, wherein said second capillary is coated.

16. The capillary column of claim 12, wherein said first and second capillaries are coated.

17. A capillary column, comprising an inlet, an outlet, a first capillary, a stationary phase packed in said first capillary, and a second capillary, wherein said second capillary is disposed partially within said first capillary, wherein said second capillary is securely positioned within said first capillary using an adhesive agent, and wherein a portion of said second capillary protrudes from said first capillary.

18. A capillary column, comprising an inlet, an outlet, a first capillary, a stationary phase packed in said first capillary, and one or more second capillaries, wherein said second capillary is disposed within said first capillary, wherein said second capillary is securely positioned within said first capillary using an adhesive agent, and wherein at least one end of the second capillary protrudes from said first capillary.

19. A method of separating one or more analytes, comprising:
    admixing said sample with an appropriate mobile phase;
    introducing said sample to a chromatography column having an inlet, an outlet, a first capillary, a stationary phase packed in said first capillary, and a second capillary, wherein said second capillary is disposed partially within said first capillary, wherein said second capillary is securely positioned within said first capillary using an adhesive agent, and wherein a portion of said second capillary protrudes from said first capillary;
    separating said analytes via said stationary phase; and
    eluting said analytes from said stationary phase using an appropriate mobile phase.

20. A method of analyzing one or more analytes, comprising:
    admixing said sample with an appropriate mobile phase;
    introducing said sample to a chromatography column having an inlet, an
    outlet, a first capillary, a stationary phase packed in said first capillary, and a second capillary, wherein said second capillary is disposed partially within said first capillary, wherein said second capillary is securely positioned within said first capillary using an adhesive agent, and wherein a portion of said second capillary protrudes from said first capillary;
    separating said analytes via said stationary phase;
    forming an eluate by eluting said analytes from said stationary phase using
    an appropriate mobile phase; and
    introducing said eluate from said second capillary into a detection system.

21. The method of claim 20, wherein said detection system is a mass spectrometer.

22. An electrospray emitter, comprising
    a first capillary,
    a stationary phase in said first capillary, and
    a second capillary,
    wherein said second capillary is disposed partially within said first sec-end capillary,
    wherein said second capillary is securely positioned within said first capillary using an adhesive agent, and
    wherein a portion of said second capillary protrudes from said first capillary.

23. The capillary column of claim 22, wherein said first capillary comprises a material selected from the group consisting of polyimide-coated fused silica, cladded fused silica, PEEKsil™, glass-lined stainless steel, ceramic glass, borosilicate glass, aluminosilicate glass, stainless steel, nickel, platinum, titanium, and polypropylene.

24. The capillary column of claim 22, wherein said second capillary comprises a material selected from the group consisting of polyimide-coated fused silica, cladded fused silica, glass-lined stainless steel, ceramic glass, borosilicate glass, aluminosilicate glass, stainless steel, nickel, platinum, titanium, and polypropylene.

25. The emitter of claim 22, wherein said first and second capillaries comprise polyimide-coated fused silica.

26. The emitter of claim 22, wherein said adhesive agent is PDMS.

27. The emitter of claim 22, wherein said second capillary protrudes from said first capillary by approximately 1 to 30 mm.

28. A method of making an electrospray emitter, comprising:
    obtaining a first capillary;
    threading a second capillary into an end portion of said first capillary, wherein said second capillary has a narrower diameter than said first capillary;
    packing said first capillary with a predetermined stationary material; and
    securing said second capillary in position within said first capillary using an adhesive agent.

29. The method of claim 28, wherein said adhesive is PDMS.

* * * * *